US006982035B1

(12) United States Patent
O'Keefe

(10) Patent No.: US 6,982,035 B1
(45) Date of Patent: Jan. 3, 2006

(54) BIPHASE ORBICULAR BIODIGESTER

(76) Inventor: David M. O'Keefe, 3714 SE. 41 Ave., Gainesville, FL (US) 32641

( * ) Notice: Subject to any disclaimer, the term of this patent is extended or adjusted under 35 U.S.C. 154(b) by 129 days.

(21) Appl. No.: 10/811,365

(22) Filed: Mar. 29, 2004

(51) Int. Cl.
C02F 3/28 (2006.01)
(52) U.S. Cl. .................. 210/258; 210/260; 210/603
(58) Field of Classification Search ............... 210/258, 210/259, 260, 603
See application file for complete search history.

(56) References Cited

U.S. PATENT DOCUMENTS

| 2,430,519 | A | * | 11/1947 | Mallory ................ 210/605 |
| 4,022,665 | A | | 5/1977 | Ghosh et al. |
| 4,323,367 | A | * | 4/1982 | Ghosh ................ 48/197 A |
| 4,396,402 | A | | 8/1983 | Ghosh |
| 4,568,457 | A | * | 2/1986 | Sullivan ............... 210/151 |
| 4,696,746 | A | | 9/1987 | Ghosh et al. |
| 5,269,634 | A | | 12/1993 | Chynoweth et al. |
| 5,525,229 | A | | 6/1996 | Shih |
| 6,342,378 | B1 | | 1/2002 | Zhang et al. |
| 2003/0033430 | A1 | | 2/2003 | Srinivasan et al. |
| 2005/0040107 | A1 | * | 2/2005 | Kasparian et al. ........ 210/636 |

FOREIGN PATENT DOCUMENTS

EP 0791561 * 2/1996

* cited by examiner

Primary Examiner—Fred G. Prince
(74) Attorney, Agent, or Firm—Sven W. Hanson

(57) ABSTRACT

An anaerobic digester is disclosed including a single orbicular vessel having two chambers configured for the separate treatment of high-solids and low-solids phases of organic matter. The vessel combines a high solids, plug flow path wherein low solids liquids are separated and directed to a high rate treatment path. The invention provides a novel and simple apparatus for the anaerobic conversion of both high solid and low solid wastes to methane, carbon dioxide, a liquid effluent that can be used as fertilizer, and a solid residue that can be used as a soil amendment. The invention combines the advantages of high solids loop digesters and low solids high rate digesters into a single orbicular vessel. Due to the orbicular geometry, in which a first chamber is a path surrounding and orbiting a second chamber, the apparatus has greater thermal and material efficiencies.

6 Claims, 4 Drawing Sheets

BIPHASE ORBICULAR BIODIGESTER

BACKGROUND OF THE INVENTION

The present invention relates to processes and apparatuses for the anaerobic digestion of organic matter, and more particularly to an orbicular vessel having two adjoining chambers for the separate treatment of high solids and low solids phases of organic matter.

Anaerobic digestion is the process by which microorganisms in an oxygen-free environment transform organic materials into biogas, nutrients, and additional cell matter, leaving salts and refractory organic matter. This process produces a source of energy while reducing the pollution potential of the waste. The biogas produced during this process is a mixture of carbon dioxide and methane (the principal component of natural gas) and may be used as a fuel. This technology is used to treat a wide variety of solid and liquid waste streams. The primary alternatives to this technology are aerobic waste water treatment for liquid waste streams and composting for solid waste streams. Anaerobic processes have advantages over aerobic waste water treatment and composting of solid waste such as reduced mixing requirements, no aeration requirements, energy production, less sludge accumulation, and lack of odor emissions.

After anaerobic treatment, most waste water is quite amenable to land application for recovery of fertilizer nutrients which are conserved by the process. Discharge of the waste to surface waters however requires further treatment to remove residual organics and nutrients. Solid residues can be land applied in a manner similar to compost.

Compared to other waste treatment technologies that require significant energy inputs, anaerobic digestion is a net producer of energy with sufficient energy produced to power the waste treatment process and meet additional energy needs. Furthermore, because anaerobic systems are air tight, the chance for odor and other gaseous pollutant emissions are negligible in comparison to aerobic processes. This also holds true for liquid emissions that are often a problem with composting technologies. Anaerobic digestion also contributes to reduction of greenhouse gas emissions. Unlike burning fossil fuels, use of waste renewable resources represents a closed carbon cycle and thus does not contribute to increases in atmospheric concentration of carbon dioxide. Anaerobic digestion can also remove heavy metals from waste streams by precipitation reactions and dechlorinate chlorinated organics.

The ability of the anaerobic process to remove organics with a minimum of sludge production and aeration demand continues to spur the development of new reactor designs applied to a variety of waste streams. Applications of the anaerobic digestion process can generally be divided into low-solids wastewater pretreatment systems and slurry or high solids systems. The slurry and high solids systems typically operate in a batch, fed-batch, or intermittently-fed mode, while low solids wastewater pretreatment systems are normally continuously fed and operated at a higher flow rate.

Recently, anaerobic wastewater pretreatment has enjoyed extensive acceptance for a variety of industrial waste waters associated with food processing, beverages, breweries, distilleries, and most recently pulp and paper production. Lagoons are the most basic application of anaerobic digestion to waste, yet they do not readily accommodate recovery of biogas. In the simplest reactor design, a continuously-fed continuously-stirred reactor (CSTR), the liquid waste is pumped through a heated tank. With this design the slow growth of the microorganisms must be compensated for by using large tanks which allow for the high hydraulic retention times (HRT= volume of digester/flow rate) of 10 to 20 days to avoid washout of the microorganisms in a CSTR. To correct for this deficiency, a number of digester designs have been developed in the prior art for various waste types. McCarty (1982) demonstrated that waste treatment in a reactor in which effluent solids are recycled is dependent on sludge age or solids retention time (SRT) rather than HRT as in a CSTR. [McCarty, P. L., (1982). *One Hundred Years of Anaerobic Treatment. Anaerobic Digestion*, 1981. Ed: D. E. Hughes, et al., Elsevier Biomedical Press B.V., Amsterdam, 3–21.] This discovery allowed him to develop the "anaerobic filter" which, like an aerobic trickling filter, uses a stationary support material to provide surface for growth of bacteria and retain them in the reactor. Lettinga (1978) developed the up flow anaerobic sludge blanket (UASB) reactor as a modification to the anaerobic filter. [Lettinga, G., (1978). *Feasibility of anaerobic digestion for the purification of industrial wastewater*, Proc. 4th European Sewage and Refuse Symp., Munich]. Van den Berg developed a hybrid anaerobic filter/sludge bed reactor. These reactors allow a HRT as low as 1 hr. [Van den Berg, L., (1985). *The downflow fixed film and upflow blanket filter reactor*. Anaerobic Digestion 1985, Proc. 4th Int. Symp. on An. Dig., Nov. 11–15, 1985, China State Biogas Association, Guangzhou, China.]

A number of designs that treat solid wastes have also been developed. These designs generally employ "cement mixer" or percolating bed approaches as exemplified in the following references: Ghosh, U.S. Pat. No. 4,396,402; Chynoweth, U.S. Pat. No. 5,269,634; Zhang, U.S. Pat. No. 6,342,378.

A digester system described by Gosh (U.S. Pat. No. 4,022,665) describes a method for the biochemical separation of anaerobic digestion into an initial acid forming or hydrolysis step and a second step in which the byproducts of this step are converted to methane. Subsequent improvements on this process (Ghosh et al U.S. Pat. No. 4,396,402, and Ghosh et al, U.S. Pat. No. 4,696,746) involved the separation of the two phases using separate vessels. U.S. Pat. No. 4,396,402 describes a leaching bed system to percolate liquid through a bed of solid waste to entrain solubulized degradation products that are then conveyed to a separate reaction vessel containing a microbial population that converts these products to methane and carbon dioxide. A portion of the treated liquid is then recycled to the leach bed to entrain further hydrolysis products. This system is similar to a system developed by Zhang et al. (U.S. Pat. No. 6,342,378) in which solid waste is leached in one vessel and the resulting leachate is processed in a second vessel. Another approach to high solids digestion employs multiple, hydraulically linked, leaching beds, as shown by Chynoweth and LeGrand in U.S. Pat. No. 5,269,634. Hall (1988) developed a three-stage system in which straw and dairy manure were treated in three vessels, each having a different maturity. [Hall, S., A. Thomas, F. Hawkes, D. Hawkes, (1988). *Operation of Linked Percolating Packed Bed AnaerobicDigesters*. In: Fifth International Symposium in Anaerobic Digestion, Bologna, Italy (1988)]. The first stage of the Hall system is a newly loaded primary reactor in which leachate is percolated through a mixture of wheat straw and dairy manure. Percolate from the primary reactor is pumped to a second reactor. Percolate from the second reactor is pumped to a third reactor, where enough methanogens have accumulated to convert the leached acids into biogas. Finally, percolate from the third reactor is pumped to the primary reactor in order to leach out more acids and inoculate the feed with methanogens. This process was adapted for the treatment of municipal solid waste (MSW) by Chynoweth and LeGrand (U.S. Pat. No. 5,269,634) in which liquid leachate is pumped between high solids leach beds of differing maturities. The operation of these multiple stage, batch reactors requires critical leachate management and complicated recirculation schemes to avoid process upset or "pickling" of the digesters through build up of organic acids and the resulting inhibition of methane formation. As is known to those skilled in the art, these systems require complex plumbing, pump systems, and controls or vigilant operator supervision to operate effectively. Furthermore, linked batch leach bed systems are only effective at treating wastes that have sufficiently recalcitrant components needed to provide physical support for biofilm production in the mature stages. Highly degradable wastes, such as food waste, will completely degrade leaving no physical support for biofilm production. This eliminates the potential for maintaining "mature batches" required to operate linked batch reactors. This limits this type of reactor to the treatment of wastes containing plastics or poorly degradable forms of paper, and plant materials such as municipal solid waste (MSW), manures containing substantial amounts of bedding, or woody and high lignin containing plant materials.

Several anaerobic digesters employ multi-baffled vessels with multiple chambers in a linear array within a single vessel (see Srinivasanand Sansalone, U.S. Patent Application 2003/0034300 A1, Shih U.S. Pat. No. 5,525,229). The ability of these digesters to treat high solids waste is dependent on the settling out of the high solids components in the first chamber and the passing of a low solids leachate through the remainder of the various chambers. However, as is known to those skilled in the art, most high solids wastes, including MSW, food waste, and manures, have some components that sink and others that float. As a result, these multi-baffled, serpentine designs can quickly become clogged with solids if used for the treatment of most high solids waste streams.

What is needed then is a simple anaerobic digester that is not susceptible to clogging and provides for separation, and independent treatment, of solid and liquid components of waste streams.

SUMMARY OF THE INVENTION

The present invention is an anaerobic digester including a single orbicular vessel having two chambers configured for the separate treatment of high solids and low solids phases of organic matter. The vessel combines a high solids, plug flow path wherein low solids liquids are separated and directed to a high rate treatment path. The invention provides a novel and simple apparatus for the anaerobic conversion of both high solid and low solid wastes to methane, carbon dioxide, a liquid effluent that can be used as fertilizer, and a solid residue that can be used as a soil amendment. The invention combines the advantages of high solids loop digesters and low solids high rate digesters into a single orbicular vessel. Due to the orbicular geometry, in which a first chamber is a path surrounding and orbiting a second chamber, the apparatus has greater thermal and material efficiencies. The apparatus geometry provides a system with multiple features to reduce or eliminate clogging and associated maintenance problems typical of the prior art. The invention also provides a flexible system, both in terms of scale of application and the variety of waste streams it can effectively treat. This digester is particularly useful for the treatment of high strength, large particle size wastes, such as source separated food waste, food processing waste, and poultry mortalities. However, it can also be used for municipal solid waste, manures, and other organic waste An object of this invention is an apparatus for the multi phase treatment of high solids wastes that does not depend on internal baffles to settle out the high solids phase from the low solids phases of the waste stream.

A further object of this invention is an apparatus that can be utilized over a wide range of scales.

A further object of this invention is an apparatus with all plumbing under negative pressure external to the tank, thus providing ease of maintenance and reducing malfunctions due to clogging.

A further object of this invention is a two-phase apparatus that does not require powered pumping and can therefore function as a two-phase system using gravity alone.

A further object of this invention is an apparatus that does not require driven mechanical devices to convey the solid phase of waste through the system.

A further object of this invention is a simple orbicular digester apparatus with high thermal efficiency such as can be can be operated at ambient temperatures or at temperatures above ambient temperatures.

A further object of this invention is an apparatus operable in a two-stage mode: the first mode, carried out in the high solids loop, being an acid or hydrolysis stage; and the second, carried out in the low solids chamber, being a methane stage.

A further object of this invention is an apparatus that can simultaneously treat multiple waste streams, both high solids and low solids, using a single vessel.

A further object of this invention is a system that has reduced susceptibility to variations in the waste stream.

Further objects and advantages of the present invention will become apparent from a consideration of the drawings and ensuing description of the preferred embodiments.

DESCRIPTION OF THE PREFERRED EMBODIMENTS

Figure 1:
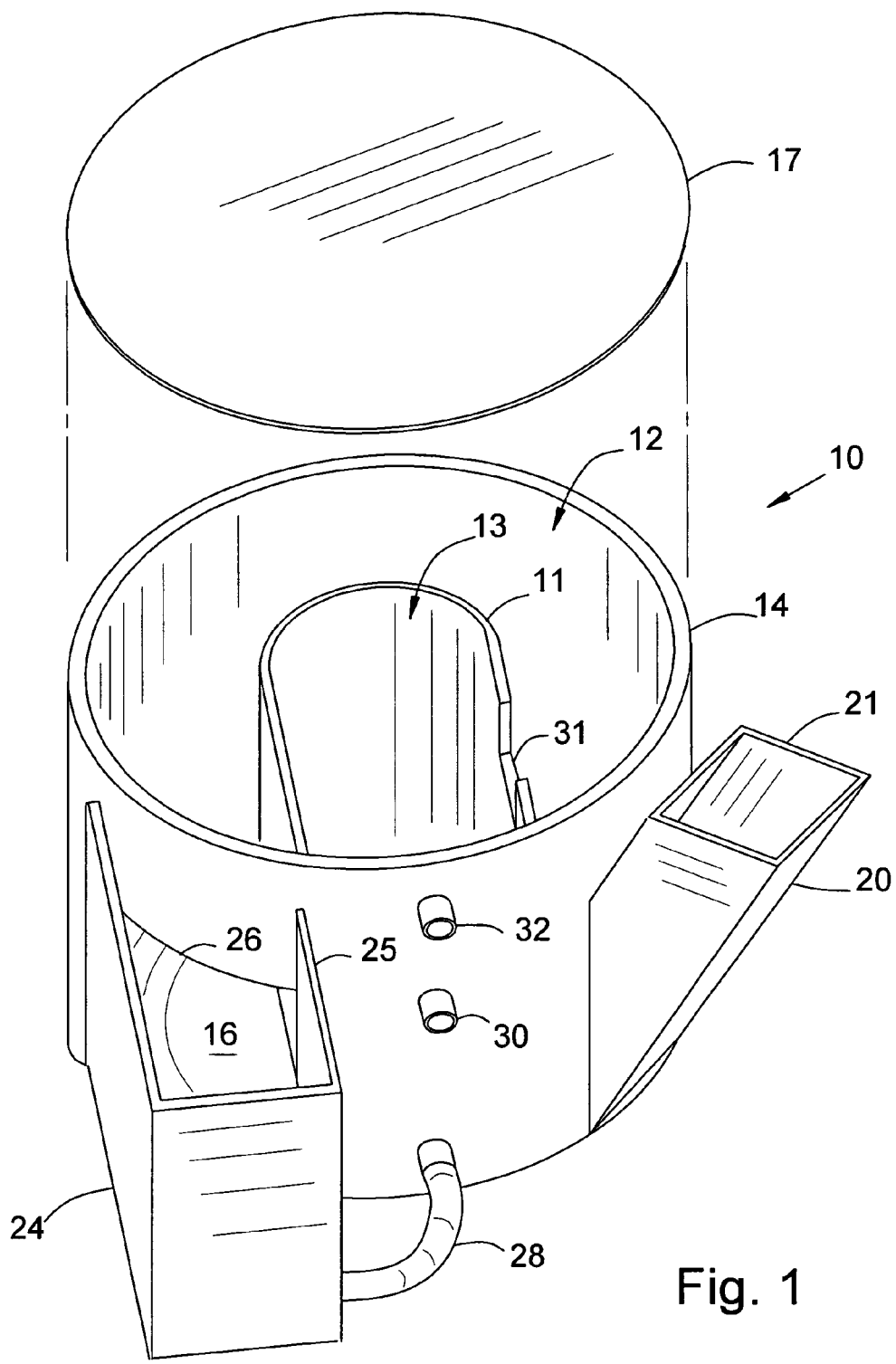
FIG. 1 is a perspective view of one embodiment of the invention.

FIG. 1 depicts, in perspective view, a preferred embodiment of the inventive apparatus. The cavity of a cylindrical digester vessel 10 is divided by an internal partition 11 into an outer, high solids loop passage 12 and an inner, low solids chamber 13. The chamber 13 is surrounded by the loop passage 12 except to the extent the chamber is bounded by the vessel outer wall 14. The vessel has an enclosing bottom 16 and opposing top 17 that, together with the outer wall and partition 11, define the space of the loop passage 12 and chamber 13. The ratio of the volume of the space of the loop passage 12 to the inner chamber 13 is preferably about 2.5 to 1.

Figure 2:
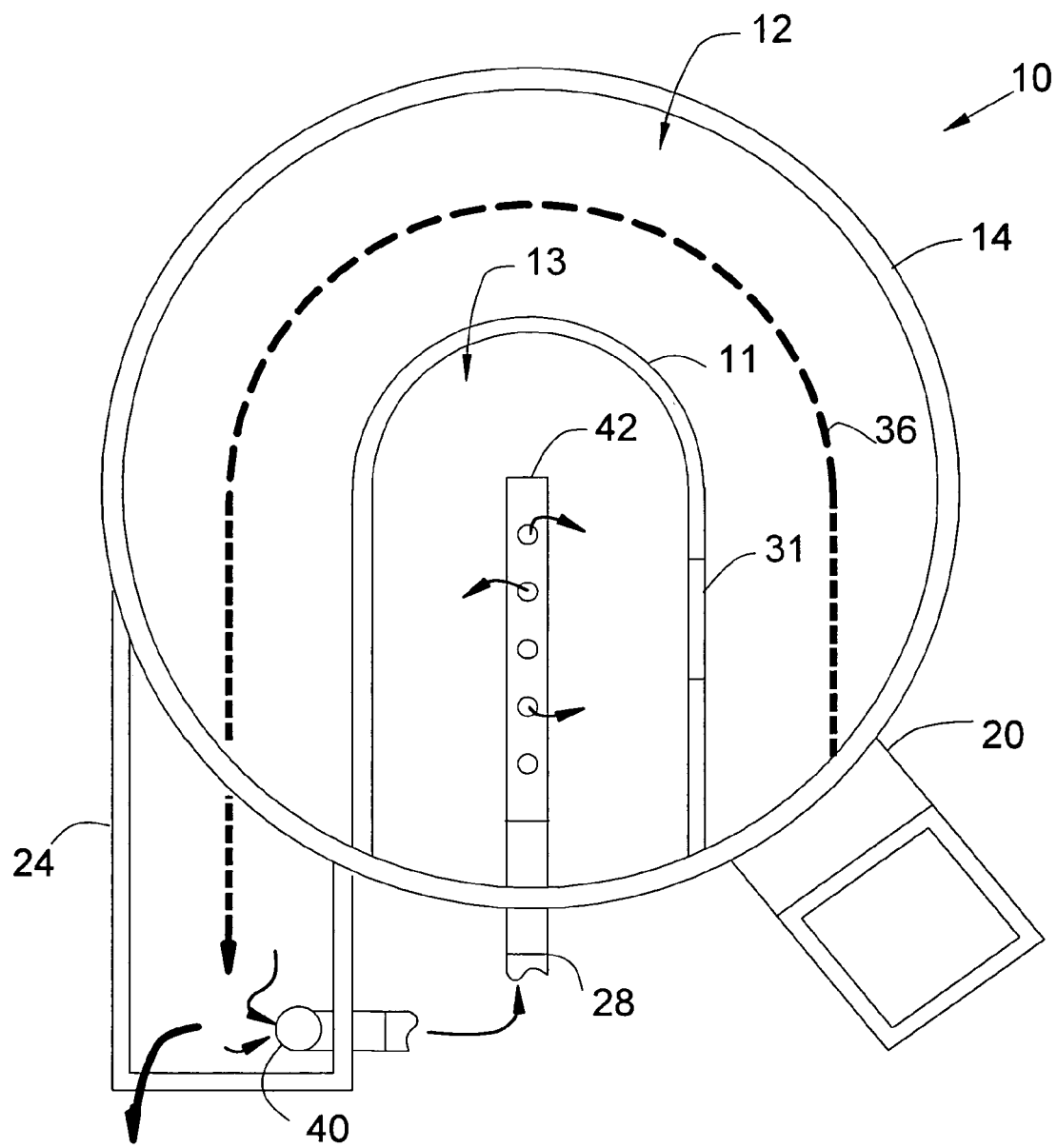
FIG. 2 is a top plan view of the embodiment of FIG. 1 including waste stream paths.

A hollow loading chute 20 penetrates the vessel wall 14 from the outside and provides a conduit from the surrounding space to one circumferential end of the loop passage 12. An upper, external, open end 21 of the loading chute 20 is preferably at a height proximate the top 17. It is critical that the open end 21 be above the top of the vessel wall penetration at the chute to enable formation of an air lock as described below. Although the chute 20 is shown as having a rectangular cross-section, this geometry is not critical. In FIGS. 1 and 2 the chute 20 is shown as intersecting the vessel wall at an approximate radial approach. More preferably, the chute 20 walls intersect and penetrate the vessel wall 14 parallel to the partition 11 and tangent to the vessel wall to form a more smooth entrance for waste entering the loop passage 12.

An effluent basin 24 penetrates the vessel wall 14 at the opposite circumferential end of the loop passage 12 from the loading chute 20. The basin 24 extends upward from the vessel bottom to near the upper extent of the vessel wall 14 and has an open access 25 at the basin top. Like the chute 20, the basin open access 25 must be above the top of the vessel wall penetration 26 to enable formation of an air lock.

The general functions of the digester elements are as follows. In operation, waste matter to be processed in the digester is introduced to the digester through the loading chute 20. Waste falls by gravity through the loading chute 20, or is forced, into the loop passage 12. The pressure of incoming waste forces the waste in the loop passage 12 along the toroidal shaped loop passage 12 to the opposite end where it is forced through the basin penetration 26 and into the basin 24. The passage time, during which the waste is retained within the loop passage, is sufficient to allow anaerobic digestion of the waste. This is controlled by the rate of waste flow. The loop passage 12 is closed to ensure an anaerobic environment. For this reason also, the external openings (20,25) of both the loading chute 20 and the basin 24 are vertically above the respective penetrations 26 through the vessel wall 14. In this manner, liquid waste may be retained at a level above the penetrations to create an air lock (see FIG. 3) to prevent ambient air from entering the vessel. Treated waste is removed from the digester via the basin opening 25.

The liquid effluent portion of the waste is collected from the basin 24 and directed through a liquid conduit 28 to the inner chamber 13 where the liquid effluent is treated separate from the waste solids. The liquid conduit may be flexible hose, rigid pipe or similar device. The inner chamber 13 may include an acclimated sludge or biofilm media following known methods of liquid waste treatment. After treatment in the inner chamber 13, the liquid waste either leaves the digester via a liquid orifice 30 or is recycled to the digester outer passage 12 via an opening and spillway 31 in the partition 11. Any generated gases leave the digester via a gas orifice 32 and can be stored and used in a variety of ways known to those skilled in the art depending on the scale and sophistication of the application.

FIG. 2 is a horizontal plan view of the embodiment of FIG. 1 with the top removed. Liquid and solid waste follows a path 36, through the loop passage 12, from the loading chute 20 to the basin 24. In this figure, a vertical liquid manifold 40 is positioned within the basin 24 and communicates through the basin, and through the liquid conduit 28, with the inner chamber 13. The vertical manifold 40 is designed to remove liquid from the basin 24 regardless of the presence and thickness of any settled or floating solids layers in the waste. Should the manifold require cleaning it may be removed from the effluent basin without needing to open the digester vessel 10. The liquid is preferably distributed in the inner chamber 13 through a horizontal manifold 42 positioned at the bottom. Less preferably, liquid waste may be collected from the basin 24, and disbursed to the inner chamber 13, via single point openings in the basin 24 and vessel wall 14 without using manifolds.

Note that the internal partition 11 is formed by a circular portion concentric with the vessel wall 14. The resulting simplicity, smoothness and lack of corners of the loop passage 12 allows movement of solid waste through the digester with a minimum of friction losses and therefore a minimum of force. Preferably, no external loading pump is employed; rather the waste is allowed to gravity feed down the loading chute 20. If necessary, the loading chute 20 may be elongated to raise its open end 21 and increase the pressure head of the waste in the loading chute 20 to speed passage through the digester.

The liquid retention time in the inner chamber can be as short as a few hours or as long as several days. If the liquid waste is not recycled from the chamber 13 to the loop passage 12, a pump is not required and the entire process can be run by gravity, an advantage in small-scale applications. The location of the liquid orifice 30 if the system is gravity fed should be below the anticipated liquid level in the basin. This may be approximated as below the top of the penetration 26. Preferably, the liquid orifice 30 is sufficiently distant from the horizontal manifold that the liquid waste cannot bypass the treatment path through the biofilm medium. If recycling of a portion of the liquid waste stream is desired, the level of the liquid in the inner chamber 13 is increased to enable the liquid to spill over the spillway 31 in the internal partition 11. This is accomplished by adding the necessary pressure head by external pumping (not shown). An external pump may be added, in-line, to the liquid conduit 28 for this purpose.

Figure 3:
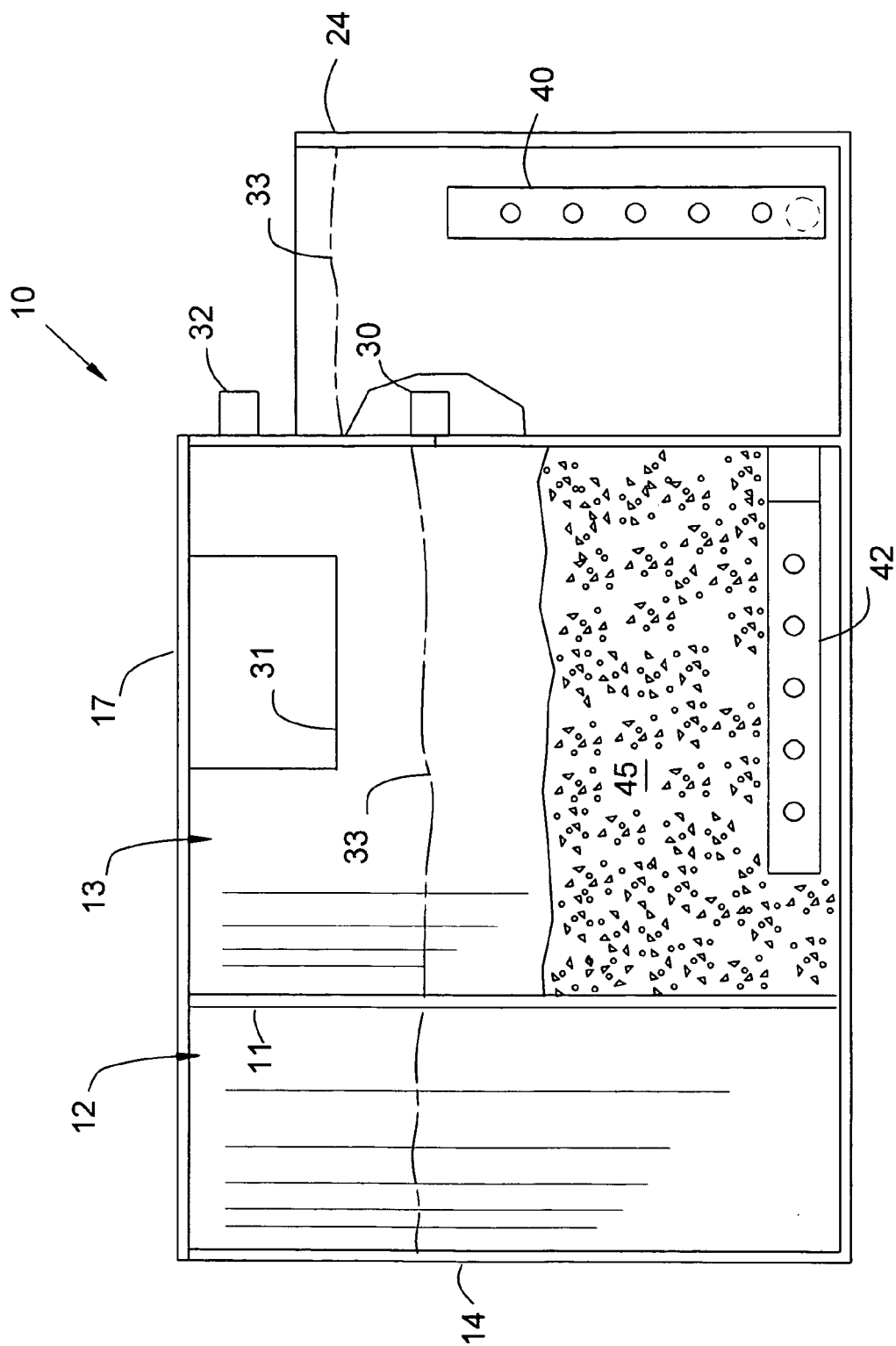
FIG. 3 is a side cutaway view of the embodiment of FIG. 1 including a particulate medium bed for liquid treatment.

FIG. 3 is a cross-section view of the digester shown in FIGS. 1 and 2 including biofilm media 45 within the inner chamber 13. The relative liquid levels 33 of liquid waste is depicted to illustrate the operation in a gravity fed mode. The anaerobic digestion processes within the digester create gases thereby increasing the pressure in the vessel 10. This internal pressure pushes down the internal liquid level which in turn increases the height of the liquid level within the basin 24. This relatively higher level drives the flow of liquid waste from the basin 24 to the inner chamber 13. Liquid waste is removed from the digester via the liquid port 30 (shown through a cutaway). In order to maintain the internal pressure the liquid port must be throttled or provided with a back pressure. This may be provided by a water column trap. For most applications, maintaining an internal pressure in the range of six to 18 inches of water column will suffice. Note that with gravity fed operation, the spillway is only used as a gas communication means between the chamber 13 and loop passage 12 while no liquid waste is so transferred.

Figure 4:
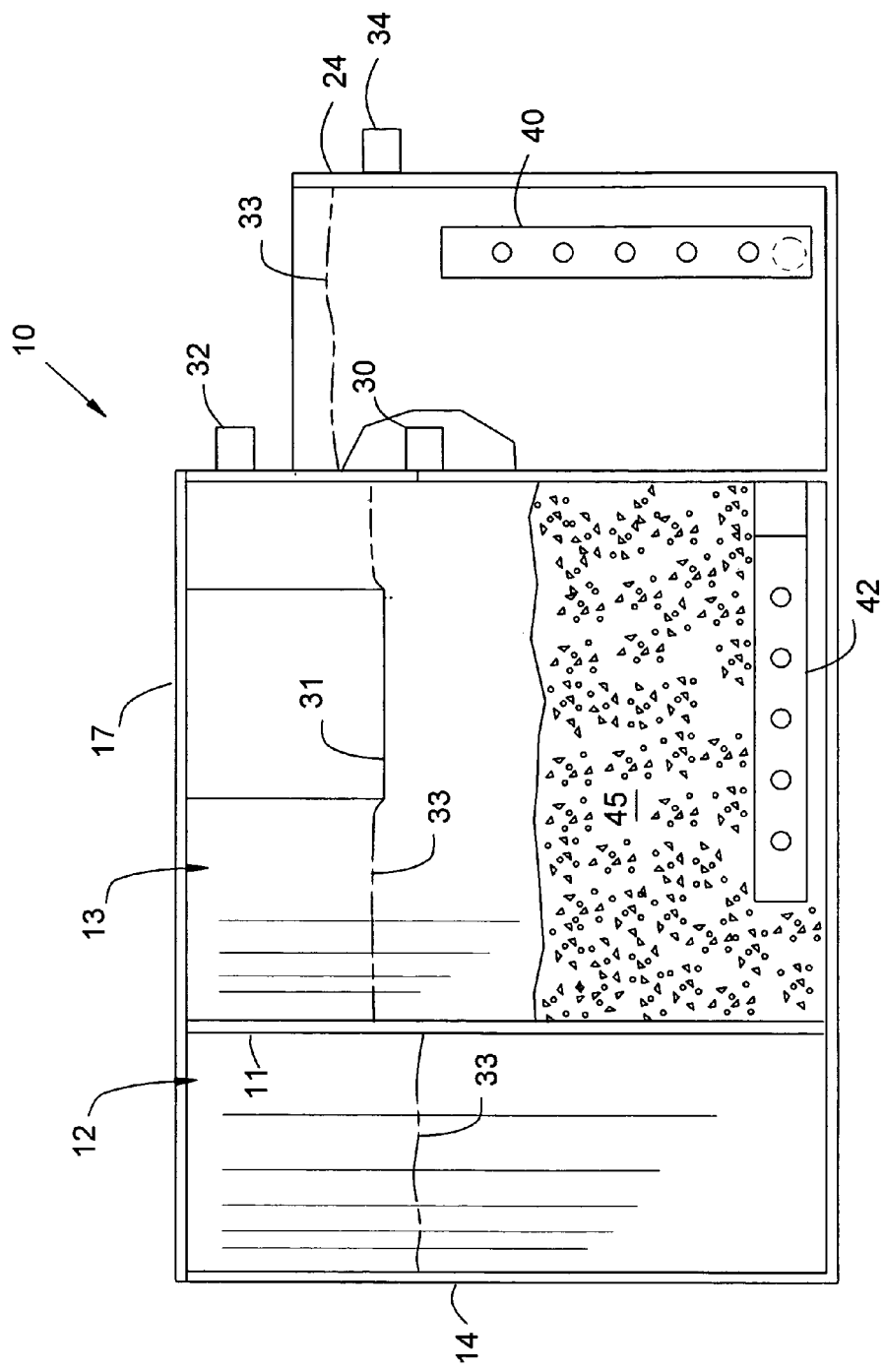
FIG. 4 is a side cutaway view of a modified embodiment including a basin liquid port for particular use with pumped recirculation of liquid waste.

FIG. 4 depicts a slightly different configuration for operation in conjunction with pumping of liquid waste for recirculation. Due to pumping, the liquid level in the chamber 13 is increased to reach the spillway 31. The liquid waste is transferred by passing over the spillway 31 and falling into the loop passage 12. Liquid waste may be withdrawn from the digester 10 from the liquid port 30 or a basin port 34. Recirculation in this manner increases the efficiency due to the more rapid movement of the liquid waste through the solid waste in the loop passage 12. The recirculated liquid also increases the alkalinity of the newly introduced waste and acts as an inoculation stream speeding, and making more thorough, the bacterial digestion of the solid portion of the waste stream. In this way, retention times of the solid waste may be reduced. For this reason, the spillway 31 is located proximate the loading chute and the start of the passage of the solid waste through the digester.

The following table provides exemplary dimensions for various applications.

| Installation | Vessel internal radius (feet) | Vessel height (feet) | Total Volume (ft$^3$) | Working Vol. (Gal.) |
|---|---|---|---|---|
| Single Residence (Kitchen waste) | 1 | 0.6 | 2 | 8 |
| Large Garden | 2 | 3 | 38 | 152 |
| 2000 Person Institution | 10 | 8 | 2500 | 10,000 |
| 1000 Head Diary | 40 | 15 | 75,400 | 300,000 |

The dimensions given are only those suggested for a typical installation of the type indicated. Actual design requirements will depend on the nature and volume of the waste stream to be treated. The working volume in the table is the total volume of waste matter contained in the vessel at one time. It is presumed that a portion of the vessel volume will contain gases produced from digestion. The particular flow rates and retention times are dependent on the particular makeup of the waste stream being processed and other variables such as ambient temperatures.

The vessel can be constructed of steel, cement, fiberglass, plastic or other materials as design parameters such as size demand. Although the internal partition 11 is shown as being the full height of the vessel walls 14, it need be only as high as needed to avoid overflow of liquid and solids between loop passage 12 and chamber 13. The top 17 for this apparatus can be rigid, flexible, or floating. In all configurations where the top 17 is removable, a pressure tight seal must be provided. For this function, the top may include a downward extending perimeter lip that fits within a water trough in the vessel body to effect a seal. This mechanism and design element is known in the industry. The loading chute 20 and the effluent basin 24 can be covered with loose-fitting covers for safety and aesthetic reasons.

The loading of waste into the digester can be assisted by screws, piston driven devices or manually, as will be appreciated by the skilled artesian, depending on the scale and sophistication of the application. The high solids components of the waste stream travel around the loop reaching the effluent basin after a period dictated by the type and amount of waste being treated. A typical solids retention time would be three to six weeks. Treated solids are removed from the effluent basin 24 using standard material handling equipment known to those skilled in the art such as belt solids separators, screws, or manual apparatus (e.g. pitchfork), depending again on the scale and sophistication of the application. In an alternative embodiment some of the treated solids can be recycled to the beginning of the high solids loop to introduce acclimated bacteria to improve reaction kinetics. Treated solids can be recycled to the beginning of the high solids loop to increase the innoculum concentration and alkalinity in the newly introduced waste.

In an alternative embodiment of the invention a heat exchanger of suitable type known to those skilled in the art can be used to heat the digester. For example, water heated from combustion of the gas produced by the digester in an electric generator or boiler can be circulated through pipes surrounding the inner chamber 13.

While the above description contains many specific design details, these should not be construed as limitations on the scope of the invention, but rather as an exemplification of preferred embodiments thereof. Inasmuch as the preceding disclosure presents the preferred embodiments devised by the inventor for practicing the invention and is intended to enable one skilled in the pertinent art to carry it out, it is apparent that other structures and methods incorporating modifications and variations will be obvious to those skilled in the art. The intended scope of the invention is defined by the following claims.

I claim:

1. An anaerobic digester comprising:
    a cylindrical vessel having an internal partition defining an orbicular loop passage and a inner chamber;
    the loop passage having a first circumferential end and a second circumferential end;
    means of communicating waste into the first circumferential end without introducing ambient air to the vessel;
    means of allowing solid waste to leave the second circumferential end without introducing ambient air to the vessel;
    means of conducting liquid waste from the second circumferential end to the inner chamber; and
    means of removing liquid from the vessel.

2. An anaerobic digester comprising:
    a vessel having a cylindrical outer wall and having an internal partition defining an orbicular loop passage and an inner chamber;
    the loop passage having a first circumferential end and a second circumferential end;
    a waste loading chute proximate the first circumferential end and communicating with the loop passage;
    an effluent basin extending from the vessel at the second circumferential end and communicating with the loop passage;
    the waste loading chute and effluent basin configured to create a vessel air lock when filled with waste; and
    a liquid conduit connecting the effluent basin and the inner chamber.

3. An anaerobic digester according to claim 2, and wherein:
    the internal partition includes a spillway opening allowing communication between the loop passage and the inner chamber.

4. An anaerobic digester according to claim 2, and wherein:
    the conduit includes pump.

5. An anaerobic digester according to claim 2, and wherein:
    the inner chamber includes biofilm media.

6. An anaerobic digester according to claim 2, and further comprising:
    a vertically oriented manifold mounted within the effluent.

* * * * *